United States Patent [19]

Hayes

[11] Patent Number: 4,659,504

[45] Date of Patent: Apr. 21, 1987

[54] PREPARATION OF PHYTATE-SALT FREE GEL DENTIFRICE

[75] Inventor: Harry Hayes, Warrington, England

[73] Assignee: Colgate-Palmolive Company, New York, N.Y.

[21] Appl. No.: 808,780

[22] Filed: Feb. 10, 1986

Related U.S. Application Data

[62] Division of Ser. No. 676,751, Nov. 30, 1984, Pat. No. 4,575,456.

[51] Int. Cl.$^4$ .......................... A61K 7/16; B01J 13/00
[52] U.S. Cl. .................................. 252/315.3; 252/314; 252/315.6; 424/49; 514/944
[58] Field of Search ...................... 424/49–58; 252/314, 315.3, 315.6; 514/944

[56] References Cited

U.S. PATENT DOCUMENTS

| | | | |
|---|---|---|---|
| 2,751,328 | 6/1956 | Sanders | 252/315.3 X |
| 3,538,230 | 11/1970 | Pader et al. | 424/50 |
| 3,959,458 | 5/1976 | Agricola et al. | 424/52 |
| 4,209,503 | 6/1980 | Shah et al. | 424/49 |
| 4,224,308 | 9/1980 | Gaffar et al. | 424/49 |
| 4,224,309 | 9/1980 | Gaffar et al. | 424/49 X |
| 4,528,181 | 7/1985 | Morton et al. | 424/49 X |
| 4,575,456 | 3/1986 | Hayes | 424/49 |

FOREIGN PATENT DOCUMENTS 2038303  7/1980  United Kingdom .

*Primary Examiner*—Richard D. Lovering
*Attorney, Agent, or Firm*—Robert L. Stone; Murray M. Grill; Herbert S. Sylvester

[57] ABSTRACT

Gel dentifrice of desirable consistency having a low water content and a hydrous silica gel polishing agent and an antinucleating agent containing at least one phosphonic group. Optimum consistency is attained by incorporating the antinucleating agent into a gel phase containing humectant and gelling agent prior to incorporation of the polishing agent therein.

4 Claims, No Drawings

PREPARATION OF PHYTATE-SALT FREE GEL DENTIFRICE

This is a division of application Ser. No. 676,751 filed Nov. 30, 1984, now U.S. Pat. No. 4,575,456 issued Mar. 11, 1986.

This invention relates to a gel dentifrice of desirable consistency.

Gel dentifrices typically contain only small amounts of water, say about 1-10% by weight and siliceous polishing material. When prepared with antinucleating agent, they tend to be thin and have runny consistencies initially and only attain firm and desirable consistencies having 48 to 72 hours or more. This delays processing and packaging and particularly makes manufacture of striped dentifrices having a visually clear or opacified gel dentifrice portion difficult.

Siliceous polishing agent is often employed in low water dentifrice gel compositions prepared for toothbrushing. Low water gel dentifrices containing such siliceous polishing agents as silica xerogel having an average particle size between about 2 and 20 microns and generally a surface area of at least about 300 $m^2/gm$, typically about 300-370 $m^2/gm$, or about 600-800 $m^2/gm$, which are described in U.S. Pat. No. 3,538,230 to Pader et al, initially tend to be thin and runny when prepared in the presence of an antinucleating agent. Similar characteristics also tend to occur when the siliceous polishing agent contains interbonded alumina in amounts up to about 10% by weight of alumina in the polishing agent.

In the present invention, use is made of a precipitated, amorphous silica gel which has been described in British Published Patent Application No. 2 038 303 A to Feig et al and in co-pending commonly assigned U.S. patent application Ser. No. 576,046, filed Feb. 1, 1984 and now U.S. Pat. No. 4,528,181 issued July 9, 1985. Such material is available from Grace G.m.b.H. as product such as Syloblanc 81, Syloblanc 81C and Syloblanc 82. It is distinct from the types of xerogel which have been sold by W. R. Grace and Co. under the trademark Syloid and which are particularly described in U.S. Pat. No. 3,538,230 to Pader et al. Indeed, although some products sold by Grace G.m.b.H. under the trademark Syloblanc were formerly or are still available under the trademark Syloid, none of Syloblanc 81, Syloblanc 81C or Syloblanc 82 have ever been available under the trademark Syloid.

It is particularly noteworthy that the grades of the silica gel employed in the present invention are less abrasive as the surface area increases whereas the grades of silica xerogel which are described in U.S. Pat. No. 3,538,230 are generally more abrasive as their surface area increases.

In the present invention the hydrous silica gel polishing agent in combination with an antinucleating agent containing at least one phosphonic group provides a low water dentifrice initially having desirable consistency. Such desirable consistency is not provided when other siliceous polishing material is employed. When the dentifrice has an initially runny consistency, it is characterized as having a generally low and poorly defined initial yield point.

It is an advantage of this invention that a low water gel dentifrice containing a hydrous silica gel and an antinucleating agent containing at least one phophonic group is provided.

It is a further advantage of this invention that a process for improving consistency of low water gel dentifrice is described.

Further advantages of the invention will be apparent from consideration of the following specification.

In accordance with certain of its aspects, this invention relates to a gel dentifrice comprising about 20-90% by weight of liquid vehicle comprising water in amount of about 1-10% by weight of said dentifrice, about 0.05-5% by weight of a gelling agent, about 10-50% by weight of a polishing agent comprising a synthetic precipitated, amorphous silica gel having an average particle size of 1 to 30 microns and (a) surface area of 1 to 600 $m^2/g$,
(b) a pore volume of 0.05 to 0.5 $cm^3/g$,
(c) a product of surface area (in $m^2/g$) × pore volume (in $cm^3/g$) less than or equal to 240,
(d) a calculated pore diameter of 1.5 to 2.5 nm and
(e) a water content of less than 25% by weight; and about 1-15% by weight of an antinucleating agent containing at least one phosphonic group.

As indicated above, the synthetic precipitated silica is of the type described in British Published Patent Application No. 2 038 303 A and U.S. patent application Ser. No. 576,046 now U.S. Pat. No. 4,528,181. Specific grades of the silica material described therein are suitable for use in the practice of the present invention. Further, specific grades which are particularly preferred are described in an October, 1980, trade publication of Grace G.m.b.H. of Norderstadt, Germany, as Syloblanc 81 and Syloblanc 82 as having the following typical physical and chemical characteristics:

|  | SYLOBLANC 81 | SYLOBLANC 82 |
|---|---|---|
| Average particle size (according to Coulter) μm | 4 | 7 |
| Wet screen residue (42 μm) % | 0.02 | 0.02 |
| pH (5% suspension in water) | 3 | 6 |
| Surface area (B.E.T.) $m^2/g$ | 400 | 480 |
| Loss on drying % | 7 | 4 |
| $SiO_2$ content (on ignited substance) % | 96 | 99 |
| Refractive index | 1.46 | 1.46 |

In a variation available as Syloblanc 81C, the pH (5% suspension in water) is about 6-8.

Syloblanc 81 and 81C, in particular are highly effective in polishing dental surfaces. Syloblanc 82 is lower in polishing effect but can be used by consumers desiring such reduced effect. Likewise, grades of the silica material may be proportioned in mixtures to produce appropriate polishing characteristics. It is noteworthy that the dentifrices are compatible in unlined aluminium dentifrice tubes even in the absence of phytate salt, which is necessary to stabilize dentifrice containing siliceous polishing agents, dual fluoride sources, and low amount of calcium ion for fluorine retention and unlined aluminum tube compatibility in the invention described in U.S. Pat. No. 4,528,181. The precipitated amorphous silica gel is employed in amount of about 10-50% by weight, typically about 10-40% in a gel dentifrice.

Aqueous slurries of the silica materials (e.g. about 5 to 20% slurries) typically have a pH of about 2 to 9. Since the dentifrice composition of the present invention preferably has a pH (measured in 20% aqueous slurry) of at least about 5.5, e.g. about 5.5-7.5, the pH of the dentifrice may be adjusted with an appropriate material such as sodium hydroxide, etc.

In the present invention, desirable consistency is provided with the presence of the antinucleating agent in amount of about 1-15% by weight, preferably about 1-5%, when the synthetic precipitated, amorphous silica gel illustrated by Syloblanc 81, Syloblanc 81C and Syloblanc 82 is present.

Antinucleating agents containing phosphonic groups have been described in the art as dentifrice components. They may provide desirable anticalculus or antiplaque effect. Typical disclosures are in U.S. Pat. Nos. 4,348,381, 4,224,309 and 4,224,308 each to Gaffar et al; U.S. Pat. No. 4,215,105 to Gaffar et al; U.S. Pat. Nos. 4,183,915 and 4,177,258 to Gaffar et al; U.S. Pat. No. 4,144,324 to Crutchfield et al; U.S. Pat. No. 4,143,128 to Kim et al; U.S. Pat. No. 4,137,303 to Gaffar et al; U.S. Pat. Nos. 4,123,512, 4,100,270, 4,098,880 and 4,042,679 to Gaffar; U.S. Pat. No. 4,064,164 to Blum et al; U.S. Pat. Nos. 4,108,962, 4,108,961, 4,034,086, 3,988,443, 3,960,888, 3,941,772 and 3,925,456 to Ploger et al; U.S. Pat. No. 3,959,458 to Agricola et al; and U.S. Pat. Nos. 4,025,616, 3,937,807 and 3,934,002 to Haefele. Amounts of about 0.01-10% by weight, preferably about 0.1-5% and most preferably about 1-3% of such antinucleating agents can be included in the dentifrice of the present invention. They include acid and non-toxic pharmaceutically acceptable salts (e.g. ammonium and alkali metal, particularly sodium of 2-phosphonobutane tricarboxylic acid-1,2,4;
phosphonoacetic acid;
alkylene diamine tetramethylene phophonic acids containing 1-10 alkylene groups;
polyalkyl bis-(phosphonomethylene)amine acid;
1,3-di-amino-alkane-1,1-diphosphonic acid as set forth in U.S. Pat. No. 4,064,164;
3-amino-1-hydroxypropane-1,1-diphosphonic acid;
azacycloalkane-2,2-diphosphonic acid containing 4-6 carbon atoms in the heterocyclic ring;
pyrrolidone-5,5-diphosphonic acid wherein the hetero-N atom is substituted with hydrogen or an alkyl group containing 1-6 carbon atoms;
azacyloalkane-2,2-diphosphonic acid wherein the hetero-N atom is substituted with hydrogen or an alkyl group containing 1-3 carbon atoms and containing 4-6 carbon atoms in the heterocylcic ring;
2-hydroxy-2-oxo-3-amino-3-phosphonyl-5-oxo-1-aza-2-phospha-cycloalkanes as set forth in U.S. Pat. No. 3,925,456;
anticalculus agents of U.S. Pat. No. 3,959,458 typified by ethane-1-hydroxy-1,1-diphosphonic acid.

Alkylene diamine tetramethylene phophonic salts, particularly lauryl sodium salts of ethylene diamine tetramethylene phosphonic acid are preferred.

The dentifrice comprises about 20-90% by weight of a liquid vehicle with a water content in the dentifrice of about 1-10% by weight. In the context of the present invention, the water content of about 1-10% is exclusive of water associated with humectant, surface-active agent solution, dye solution, water of hydration, etc. Most of the liquid phase is humectant. The liquid phase is characterized as having a refractive index of about 1.45 to 1.47, close to that of the hydrous silica gel. The low water gel dentifrice is visually substantially clear or would be substantially clear except for the presence of an opacifying agent, such as titanium dioxide. Typical humectants include glycerine, sorbitol (e.g. 70% solution), maltitol (e.g. 70-75% solution), and mixtures thereof. Water associated with the humectants may be present in addition to the separate water content set forth above.

The dentifrice also contains a gelling or binding agent as a solid vehicle agent, although this may be in small amount, since the synthetic, precipitated silica can effect a thickening or gelling of the dentifrice into a creamy or pasty consistency. Gelling or binding agents include alkali metal carboxymethyl cellulose, xanthan, Irish moss, iota-carrageenan, gum tragacanth, hydroxyethyl cellulose, hydroxypropyl cellulose, polyvinyl pyrrolidone, starch and mixtures thereof. Alkali metal carboxymethyl cellulose, such as sodium carboxymethyl cellulose, is preferred. Gelling agents may be used in amount of about 0.05-5% by weight, typically about 0.05-2% and preferably about 0.1-1.5%.

Any suitable surface active or detersive material may be included in the dentifrice compositions. Such compatible materials are desirable to provide additional detersive foaming and antibacterial properties depending upon the specific type of surface active material and are selected similarly. These detergents are water-soluble compound usually, and may be anionic, nonionic, amphoteric or cationic in structure. It is usually preferred to use the water-soluble non-soap or synthetic organic detergents. Suitable detersive materials are known and include, for example, the water-soluble salts of higher fatty acid monoglyceride monosulphate detergent (e.g. sodium coconut fatty acid monoglyceride monosulphate), higher alkyl sulphate (e.g. sodium lauryl sulphate), alkyl aryl sulphonate (e.g. sodium dodecyl benzene sulphonate, higher fatty acid esters of 1,2-dihydroxy propane sulphonate) and the like.

Further surface active agents include the substantially saturated higher aliphatic acyl amides of lower aliphatic amoino carboxylic acid compounds, such as those having 12 to 16 carbons in the acyl radical. The amino acid portion is derived generally from the lower aliphatic saturated monoaminocarboxylic acid compounds. Suitable compounds are the fatty acid amides of glycine, sarcosine, alanine, 3-aminopropanoic acid and valine having about 12 to 16 carbons in the acyl group. It is preferred to use the N-lauroyl, myristoyl and palmitoyl sarcoside compounds, however, for optimum effects.

The amide compounds may be employed in the form of the free acid or preferably as the water-soluble salts thereof, such as the alkali metal, ammonium, amine and alkylolamine salts. Specific examples thereof are the sodium and potassium N-lauroyl, myristoyl and palmitoyl sarcosides, ammonium and ethanolamine N-lauroyl glycide and alanine. For convenience herein, reference to "amino carboxylic acid compound," "sarcoside," and the like refers to such compounds having a free carboxylic group or the water-soluble carboxylate salts.

Such materials are utilized in pure or substantially pure form. They should be as free as practicable from soap or similar higher fatty acid material which tends to reduce the activity of these compounds. In usual practice, the amount of such higher fatty acid material is less than 15% by weight of the amide and insufficient to substantially adversely affect it, and preferably less than about 10% of said amide material.

Other particularly suitable surface-active materials include nonionic agents such as condensates of sorbitan monostearate with approximately 20 moles of ethylene oxide, condensates of ethylene oxide with propylene oxide, condensates of propylene glycol ("Pluronic"

materials) and amphorteic agents such as long chain (alkyl)amide-alkylenealkalated amine derivatives, which are available under the trademark "Miranol" C₂M. Cationic surface active germicides and antibacterial compounds such as diisobutylphenoxyethyoxyethyl dimethyl benzyl ammonium chloride, benzyl dimethyl stearyl ammonium chloride, tertiary amines having one fatty alkyl group (of from 12–18 carbon atoms) and two (poly)oxyethylene groups attached to the nitrogen (typically containing a total of from about 2 to 50 ethanoxy groups per molecule) and salts thereof with acids, and compounds of the structure

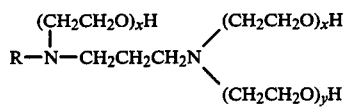

wherein R represents a fatty alkyl group containing from about 12 to 18 carbon atoms, and x, y and z total 3 or higher, as well as salts thereof with mineral or organic acids, may also be used. It is preferred to use from about 0.05 to 5% by weight of the foregoing surface-active materials in the oral preparation of the present invention.

The compositions of the present invention may also contain a fluorine-containing compound having a beneficial effect on the care and hygiene of the oral cavity, e.g., diminution of enamel solubility in acid and protection of the teeth against decay which do not substantially detract from the clarity of the dentifrice. Examples of known fluorine materials include sodium fluoride, potassium fluoride, stannous fluoride, stannous chlorofluoride, potassium stannous fluoride ($SnF_2KF$), and complex fluorides such as sodium fluorozirconate and particularly sodium monofluorophosphate. These materials, which dissociate or release fluorine-containing ions, suitably may be present in an effective but non-toxic amount, usually within the range of about 0.01 to 1% by weight of the water-soluble fluorine content thereof. Sodium fluoride and sodium monofluorophosphate are particularly preferred, as well as mixtures thereof.

Various other materials may be incorporated in the dental creams of this invention. Examples thereof are opacifiers, preservatives, stabilizers, silicones, chlorophyll compounds and ammoniated materials such as urea, diammonium phosphate and mixtures thereof. These adjuvants are incorporated in the instant compositions in amounts which do not substantially adversely affect the desired properties and characteristics and are suitably selected and used in conventional amounts.

For some purposes it may be desirable to include antibacterial agents in the compositions of the present invention. Typical antibacterial agents which may be used in amount of about 0.01% to about 5%, preferably about 0.05 to about 1.0%, by weight of the dentifrice composition include cetyl pyridinium chloride, benzethonium chloride as well as:

$N^1$-4 (chlorobenzyl)-$N^5$-(2,4-dichlorobenzyl)biguanide;
p-chlorophenyl biguanide;
4-chlorobenzhydryl biguanide;
4-chlorobenzhydrylguanylurea;
N-3-lauroxypropyl-$N^5$-p-chlorobenzylbiguanide;
1,6-di-p-chlorophenylbiguanidohexane;
1-(lauryldimethylammonium)-8-(p-chlorobenzyldimethylammonium) 5,6-dichloro-2-guanidinobenzimidazole;
$N^1$-p-chlorophenyl-$N^5$-laurylbiguanide;
5-amino-1,3-bis(2-ethylhexyl)-5-methylhexahydropyrimidine; and their non-toxic addition salts.

Any suitable flavouring or sweetening materials may be employed in formulating a flavour for the compositions of the present invention. Examples of suitable flavouring constituents include the flavouring oils, e.g. oils of spearmint, peppermint, wintergreen, sassafras, clove, sage, eucalyptus, marjoram, cinnamon, lemon and orange, as well as methyl salicylate. Suitable sweetening agents include sucrose, lactose, maltose, sorbitol, sodium cyclamate, sodium saccharine, dipeptides of U.S. Pat. No. 3,939,261 and oxathiazin salts of U.S. Pat. No. 3,932,606. Suitable flavor and sweetening agents may together comprise from about 0.01 to 5% or more of the composition.

The dentifrice is packaged in a container from which it can be readily extruded such as a pressure differential or mechanically operated dental cream dispenser or a lined or unlined aluminium tube or wax lined lead tube or plastic tube, which may be laminated with aluminium. It may be employed as a complete dentifrice or as a stripe within or on the surface of a similarly formulated but contrasting dentifrice or a stripe in conjunction with a substantially different dentifrice formulation.

The dentifrice is most desirably prepared in order to attain optimum, desirable consistency by forming a premix of the gelling agent with the liquid vehicle components, e.g. water and humectant adding thereto the antinucleating agent containing at least one phosphonate group and then blending therewith the hydrous silica gel. If employed, additional ingredients such as surface active agents may then be added. In processing, the hydrous silica gel is not added before the antinucleating agent.

Although the invention is described with regard to the illustrative example, it will be apparent to one skilled in the art that various modifications may be made thereto which fall within its scope. All amounts are by weight unless otherwise indicated.

EXAMPLE 1

The following opacified gel dentifrice is prepared and placed in an unlined aluminium tube:

| PART Ia | |
|---|---|
| Glycerine | 17.000 |
| Sorbitol (70%) | 42.900 |
| Sodium carboxymethyl cellulose | 0.300 |
| Sodium saccharin | 0.200 |
| Sodium fluoride | 0.220 |
| Titanium dioxide | 1.000 |
| PART Ib | |
| Water | 5.000 |
| Ethylene diamine tetra-methylene phosphonic acid | 1.870 |
| Sodium hydroxide | 0.750 |
| PART II | |
| Precipitated amorphous hydrous silica gel* | 20.000 |
| PART III | |
| Sodium lauryl sulphate | 1.760 |
| Glycerine (supplemental addition) | 8.000 |
| PART IV | |
| Flavour | 1.000 |

| | |
|---|---|
| -continued | |
| pH (20% slurry) | 7.0 |

*Syloblanc 81 available from Grace G.m.b.H.;

The dentifrice is prepared as an opacified gel by forming a preblend of the humectants, gelling agent, sweetener, fluoride, and opacifier corresponding to Part Ia, mixing Part Ib containing low water content for the dentifrice and partially neutralized antinucleating agent. The heat of neutralisation produced in this mixing step alleviates the need to apply an external heat source, thereby providing an efficient low-cost method of dentifrice formation. The hydrous silica gel polishing agent (Part II) is then added followed by mixing therewith additional minor amount of a humectant and the surface active agent (Part III) and then the flavor (Part IV).

The low water opacified gel dentifrice has desirable consistency upon formulation. When the preparation procedure is modified, the rheology is less than optimum but still quite desirable, particularly compared to corresponding dentifrice formulations prepared with other siliceous polishing agents, even when supplemented with an additional thickening ingredient.

The illustrated dentifrice can be modified with similar rheological results by replacing the partially neutralized ethylene diamine tetramethylene phosphonic acid with other antinucleating agents including sodium salts of 2-phosphonobutane tricarboxylic acid-1,2,4 and ethane-1-hydroxy-1,1-diphosphonic acid.

In accordance with further modifications, Syloblanc 81 can be replaced by Syloblanc 81C, Syloblanc 82 and a 1: mixture of Syloblanc 81 and 82.

In the example sodium cyclamate may replace sodium saccharin.

It will be apparent to those skilled in the art that further modifications of the examples illustrative of the invention may be made thereto.

I claim:

1. The process of preparing a phytate-salt free gel dentifrice consisting essentially of forming a preblend of a liquid vehicle containing humectant and a gelling agent, mixing therewith an antinucleating agent containing at least one phosphonic group and adding thereto a polishing agent comprising a synthetic precipitated, amorphous silica gel having an average particle size of 1 to 30 microns and
   (a) a surface area of 1 to 600 $m^2/g$,
   (b) a pore volume of 0.05 to 0.5 $cm^3/g$,
   (c) a product of surface area (in $m^2/g$) $\times$ pore volume (in $cm^3/g$) less than or equal to 240,
   (d) a calculated pore diameter of 1.5 to 2.5 nm
and said dentifrice consisting essentially of said liquid vehicle in amount of about 20–90% by weight and including water in amount of about 1–10% by weight, about 0.2–5% by weight of said gelling agent, about 10–50% by weight of said polishing agent and about 1–15% by weight of said antinucleating agent.

2. The process of preparing a gel dentifrice claimed in claim 1 wherein said antinucleating agent is ethylene diamine tetramethylene phosphonic acid or non-toxic pharmaceutically acceptable salt thereof.

3. The process of preparing a gel dentifrice claimed in claim 2 wherein said antinucleating agent is a neutralised ethylene diamine tetramethylene phosphonic acid.

4. The process of preparing a gel dentifrice claimed in claim 1 wherein said synthetic amorphous silica gel is selected from the group having characteristics consisting of:

| | a | b | c |
|---|---|---|---|
| Average particle size (according to Coulter) μm | 4 | 7 | 4 |
| Wet screen residue (42 μm) % | 0.02 | 0.02 | 0.02 |
| pH (5% suspension in water) | 3 | 6 | 6–8 |
| Surface area (B.E.T.) $m^2/g$ | 7 | 4 | 7 |
| Loss in drying % | 7 | 4 | 7 |
| $SiO_2$ content (on ignited substance) | 96 | 99 | 96 |
| Refractive index | 1.46 | 1.46 | 1.46 | and (d) mixtures thereof

* * * * *